United States Patent [19]

Baurmash

[11] Patent Number: 4,904,188
[45] Date of Patent: Feb. 27, 1990

[54] DIRECT BONDED ARCH BAR FOR MAXILLO-MANDIBULAR INJURIES

[76] Inventor: Harold Baurmash, 1600 Parker Ave., Fort Lee, N.J. 07024

[21] Appl. No.: 196,735

[22] Filed: May 20, 1988

[51] Int. Cl.⁴ ............................................. A61C 5/00
[52] U.S. Cl. .................................... 433/215; 128/861; 128/9
[58] Field of Search ............................ 433/215, 9, 89; 128/861

[56] References Cited

U.S. PATENT DOCUMENTS 4,063,360 12/1977 Waller .................................... 433/9
4,165,561  8/1979 Miller et al. ............................ 433/9
4,230,104 10/1980 Richter ............................... 128/89 A
4,749,352  6/1988 Nicholson ............................... 433/9

Primary Examiner—Robert Peshock
Attorney, Agent, or Firm—James L. Jackson & Associates

[57] ABSTRACT

An arch bar for direct bonding to the teeth of a patient comprises an elongated arch bar having a plurality of ligature hook elements extending from one side thereof. The back or gingival portion of the arch bar is provided with a layer of mesh material extending substantially the entire length thereof. The mesh material may be in the form of a fine metal mesh which is spot welded or otherwise secured to the gingival portion of the arch bar to effect optimum retention with the bonding agent that secures the arch bar to the enamel surfaces of the patient's teeth. The arch bar may be perforate along its length to enable light passage through the arch bar when photo polymerizing bonding agents are employed. The ligature hooks may be of a configuration to enable retention thereof by special application instruments for positioning of the arch bar during installation.

15 Claims, 1 Drawing Sheet

DIRECT BONDED ARCH BAR FOR MAXILLO-MANDIBULAR INJURIES

FIELD OF THE INVENTION

This invention relates generally to arch bars that are typically utilized for the management of maxillo-mandibular bone injuries. More particularly, the invention is directed to an arch bar construction that is adapted for direct bonding to the teeth of a patient to provide retention capabilities sufficient for maintaining intermaxillary fixation. Even more specifically, this invention is directed to an arch bar construction that is backed by a bonding base in the form of a mesh base for bonded attachment of the arch bar to the enamel surfaces of the patient's teeth.

BACKGROUND OF THE INVENTION

The arch bar has been the mainstay for the management of maxillo-mandibular bone injuries for an extensive period of time. The originators of such arch bars and their method of use, Sauer in Germany and Gilmer in the United States, utilized an ordinary round bar which was ligated to the teeth of the patient by means of brass ligature wires. Subsequently, a modification of the original arch bar technique by Blair and Ivey resulted in a bar flattened on one side and about 2 mm in width to conform better to the teeth and provide greater stability. Little has changed since the introduction of this arch bar. In spite of its simplicity and reliability, there are numerous problems associated with its utilization.

The application of the arch bar via circumdental wiring, requires local anesthesia regardless of the location of the fracture and is often time consuming and uncomfortable for the patient. Furthermore, securing the arch bar to isolated posterior teeth can be difficult. One of the main failings of the bar technique results from improper adaptation of the appliance whereby teeth may be moved orthodontically in a lateral or extrusive direction. The incisor teeth are the most vulnerable.

Periodontal injury is always a threat since the wires must often be placed below the gingival margins in order to guarantee stability and with tightening there is a tendency for the appliance to be displaced apioally, resulting in gingival impingement. With the inherent difficulty of maintaining proper oral hygiene and the necessity at times to penetrate the interdental papilla with the circumdental wire when there are tight interproximal embrasures, some degree of gingival inflammation and damage can be expected.

In cases of mandibular fractures, the actual tightening of the wires to the arch bar may be injurious. During this procedure, constant tension must be applied to the wire and occasionally a hard pull must be given to the wire take up the slack, further distracting the fracture margins and possibly complicating the displacement.

The acid etch technique developed by Buonocore, using orthophosphoric acid in 1955 established the foundation for direct bonding procedures for orthodontic brackets. In 1970 Retief, et al. reported on the direct bonding of orthodontic attachments and in 1978 the acid etch and direct bonding technique for orthodontic brackets was acknowledged in a publication by Newman. The present invention involves an extension of the acid etch and direct bonding techniques to arch bars, thus achieving improvements in maxillo-mandibular surgical procedures.

It is therefore a feature of the present invention to provide a novel arch bar construction facilitating direct bonding of arch bars to the teeth of patients to facilitate the management of maxillo-mandibular injuries.

It is another feature of this invention to provide a novel arch bar construction enabling efficient bonding of the arch bar to the teeth of the patient by means of photopolymerizing bonding agent for positive assurance of arch bar placement prior to setting of the bond by application of light to the bonding agent.

It is also a feature of this invention to provide a novel arch bar construction incorporating a mesh backing for the arch bar that provides efficient retention of the arch bar to the bonding agent.

Other and further features of this invention will become obvious upon a review of the disclosure embodied herewith.

SUMMARY OF THE INVENTION

An arch bar for direct bonding to the teeth of a patient for the management of maxillo-mandibular injuries incorporates an elongated arch bar forming facial, lingual occlusal and gingival portions and being capable of conforming to the configuration of a portion of an alevolar arch of the patient. A plurality of ligature hook elements extend from the gingival portion of the arch bar and project in spaced relation with the facial portion of the arch bar. These ligature hook elements extend toward the occlusal portion of the arch bar to enable intermaxillary ligation between opposed arch bars by means of ligature wires or elastic ligature elements. A layer of mesh material is adhered to the lingual portion of the arch bar and directly contacts the enamel surfaces of the patient's teeth when the arch bar is in position. This layer of mesh functions as a bonding base for bonded fixation of the arch bar to the enamel surfaces of the patient's teeth. The mesh material may be composed of any suitable material capable of establishing an appropriate bond or mechanically interlocking relation with the bonding agent utilized for securing the arch bar to the teeth of the patient. For example, the mesh material may be composed of metal and may be spot welded, brazed or welded to the arch bar such that it is positively fixed in place. The bonding agent establishes efficient mechanical retention with the layer of mesh and thereby secures the arch bar sufficiently firm to withstand intermaxillary fixation.

When photopolymerizing type bonding agent is employed for fixing the arch bar to the teeth of the patient, the arch bar may have a perforate form defined by numerous apertures positioned along its length. After the arch bar has been properly placed and is in contact with the bonding agent on the patient's teeth, light of appropriate wavelength, including visible light, ultraviolet light, etc. may be applied through these apertures to the bonding agent, thereby causing efficient polymerization thereof. In essence the apertures facilitate more rapid light induced polymerization of the bonding agent than would otherwise be attainable and thus provides the surgeon with a better degree of control during the surgical procedure.

The ligature hook elements may be of rectangular form to enable the arch bar to be secured and placed by means of an arch bar application instrument.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
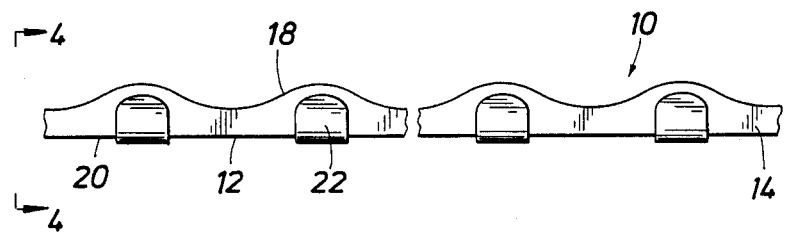
FIG. 1 is an elevational view of an arch bar constructed in accordance with the present invention and adapted for direct bonding to the teeth of the patient.
Figure 5:
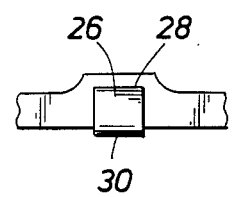
FIG. 5 is a fragmentary elevational view of a portion of the arch bar representing a modified embodiment of this invention.

Referring now to the drawings and first to FIG. 1 an archwire construction is demonstrated generally at 10 incorporates an elongated arch bar 12 which, for purposes of reference, defines a facial portion 14, a lingual portion 16, a gingival portion 18 and an occlusal portion 20. A plurality of ligature hooks 22 extend from the arch bar and are disposed in spaced relation with the facial portion such that ligature slots 24 are defined between the ligature hooks and the facial portion. The ligature hooks may be fixed to the arch bar in any suitable manner; preferably, however, the ligature hooks are formed integrally with the arch bar which is stamped from a sheet of metal or other suitable material and are bent to the configuration illustrated in the drawings. The ligature hook elements 22 may be of the form shown in FIG. 2, defining the arcuate upper surfaces to minimize trauma to the facial tissues. In the alternative, the ligature hook elements may take the form shown at 26 in FIG. 5 defining a generally rectangular configuration forming upper and lower generally parallel surfaces 28 and 30 that enable one or more of the ligature hooks to be firmly grasped by means of a special application instrument. In such case, the instrument would be utilized for efficient placement of the arch bar in relation to the teeth of the patient so that the arch bar will be properly placed prior to polymerization of the photo curing bonding agent.

Figure 2:
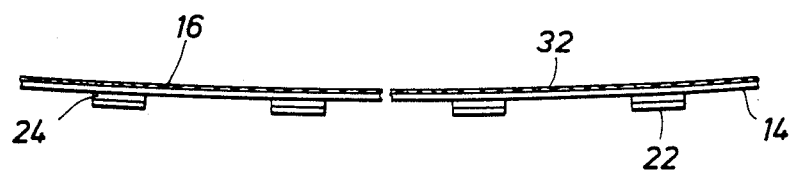
FIG. 2 is a plan view of the arch bar construction of FIG. 1.
Figure 3:
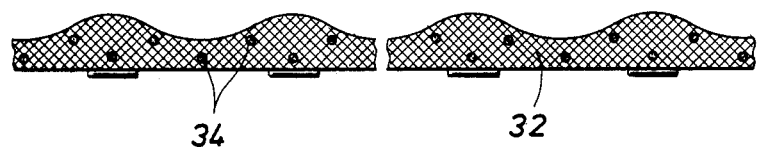
FIG. 3 is a rear elevational view of the arch bar of FIGS. 1 and 2, illustrating the lingual surface preparation of the arch bar for efficient direct bonding activities.
Figure 4:
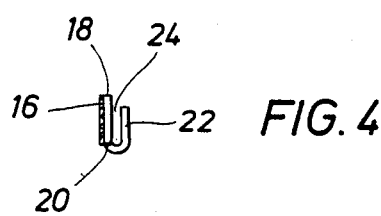
FIG. 4 is an end view of the arch bar construction of FIGS. 1-3.

As shown particularly in FIGS. 2, 3 and 4 the back or lingual portion of the elongated arch bar is provided with a layer of mesh 32 which provides the lingual portion of the arch bar with a surface capable of establishing mechanical interlocking with the bonding agent that is utilized to secure the arch bar to the teeth of the patient. This mesh material may be in the form of a screen formed by woven screen elements and which is adhered to the lingual portion of the archwire in any suitable manner. Preferably, the mesh is in the form of a wire mesh which is secured to the lingual portion of the elongated arch bar by means of spot welding, welding, braizing or soldering. As shown in FIG. 3 the mesh 32 extends substantially throughout the entire length of the elongated arch bar and is secured to the arch bar by means of a plurality of spot welds 34. The spot welded wire mesh 52 is securely fixed to the lingual portion of the elongated arch bar and establishes efficient mechanical interlocking relation with the bonding agent. Thus, the arch bar is capable of being firmly secured to the enamel surfaces of the patient's teeth with sufficient structural integrity to withstand intermaxillary fixation.

Figure 6:
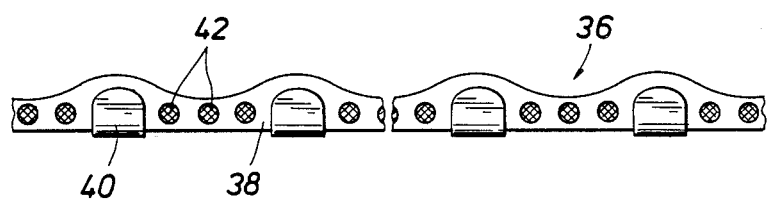
FIG. 6 is an elevational view of an arch bar constructed in accordance with the present invention and being provided with a plurality of apertures to enable efficient passage of light through the arch bar for photopolymerization of the bonding agent.

Referring now to FIG. 6, an alternative embodiment of the present invention is provided wherein an elongated direct bonding arch bar is shown generally at 36 and defines an elongated arch bar 38 having a plurality of ligating hooks 40 projecting therefrom in the same manner as discussed above in connection with FIGS. 1-4. The elongated arch bar 32 is backed by a layer of mesh in the same manner as shown in FIGS. 2 and 3. The arch bar 38 is formed to define a plurality of apertures 42 positioned in spaced relation along substantially the entire length of the arch bar. The apertures 42 may have a dimension up to about 50% of the width of the arch bar. When photopolymerization type bonding agent is employed to fix the arch bar to the patient's teeth, light of suitable wavelength may be passed through the apertures 42 into the bonding agent to thus positively insure fast and efficient polymerization of the bonding agent and thus positive and efficient fixation of the arch bar in bonded assembly with the teeth of the patient. Moreover, the surgeon will have better control of polymerization since a light gun can be used in controlled manner to achieve the degree of fixation that is desired. As an example, with the arch bar held in place manually or by an application instrument, light can be applied in short increments to "tack" the arch bar in place. After the proper position of the arch bar has been verified, light of greater duration may be applied for complete polymerization of the bonding agent.

Through utilization of a mesh backed arch bar bonded to the teeth of the patient in the manner discussed above, many of the problems associated with conventional arch bars are overcome. Such an appliance would be more hygienic: less traumatic to the gingiva and periodontal structures, would not require adjustment or tightening during treatment; could be applied painlessly without disturbance to the fracture sites and would not result in abnormal tooth movement. In addition, its application and removal should be more rapid and noninvasive.

EXAMPLE

In order to compare a conventional arch bar with a mesh backed arch bar constructed in accordance with the present invention, a patient with a left angle fracture (through an unerupted third molar) associated with a mild left posterior open bite received a segmented three piece bonded arch bar in the maxilla and a conventionally wired Erich arch bar in the mandibal. Intermaxillary elastics were placed initially to correct the malocclusion and then replaced with intermaxillary wires. The mandibular arch bar required tightening on three occasions during the five week period of immobilization and at the time of removal there was significant difference in the general state of the gingival tissues of the upper and lower jaws.

This type of appliance compliments the placement of compression or non-compression plates since the teeth must be fixed in occlusion during their placement, followed by intermaxillary fixation for a short period thereafter. Dentoalveolar fractures, avulsed and transplanted teeth can also be efficiently stabilized according to the principles of this invention.

It is recommended that arch bars according to the present invention be applied in segments to insure the best tooth adaptation and bonding. The segments would include first bicuspid to first molar and the six anterior teeth (preferably in the mandibal) or cuspid to first molar and four anterior teeth (satisfactory in the maxilla). Displaced mandibular body fractures would require modification in order to avoid crossing the fracture line. However, once reduction is obtained either through intermaxillary elastics or open reduction, the segmented arch bars could be bonded together.

As with all bonding, in addition to being completely dry, the enamel surface must be free of plaque. This can be accomplished with pumice or by scrubbing the teeth with chlorohexidene. An etching gel rather than liquid orthophosphoric acid is advantageous in that it remains on the teeth rather than dripping onto the gingiva which might result in a chemical burn. In the bonding of metal brackets to the teeth, it has been found that filled diacrolate resins of the BisGMA type have outstanding physical properties and are generally stronger than the other groups. In a study of tensile bond strengths of orthodontic bonding resins, it has been determined although the tensile bond strengths of the bonded brackets is always greater after 24 hours than those after 15 minutes. The results suggested that orthodontic wires would be placed 15 minutes after completion of the bonding procedure. It is therefore suggested that a minimum period of 15 minutes should elapse before intermaxillary fixation is instituted. Where open reduction is indicated, it might be advisable to bond the arch bars to the teeth 24 hours prior to surgery for better bonding and shorter operating time.

While the foregoing is directed to the preferred embodiment, the scope is determined by the claims which follow:

What is claimed:

1. An arch bar for direct bonding to the teeth of a patient for the management of maxillo-mandibular injuries, comprising:
   (a) an elongated arch bar forming facial, lingual, occlusal and gingival portions thereof and being capable of conforming to the configuration of at least a portion of the buccal and facial surfaces of the teeth of an alveolar arch of the patient and further adapted for contact with a plurality of said teeth;
   (b) a plurality of ligature hook elements extending from said occlusal portion and projecting in spaced relation with said facial portion and extending toward the gingival; and
   (c) a substantially continuous elongated strip of mesh material being adhered to said lingual portion of said arch bar and extending substantially along the entire length of said lingual portion and functioning as a bonding base for bonded fixation of said arch bar to the teeth of the patient.

2. An arch bar as recited in claim 1, wherein:
said elongated strip of mesh is composed of metal.

3. An arch bar as recited in claim 2, wherein:
said elongated strip of mesh is adhered to said arch bar by spot welding.

4. An arch bar as recited in claim 2, wherein:
said elongated strip of mesh is adhered to said arch bar by welding.

5. An arch bar as recited in claim 2, wherein:
said elongated strip of mesh is adhered to said arch bar by soldering.

6. An arch bar as recited in claim 1, wherein:
said plurality of ligature hooks are of generally rectangular form to enable secured engagement thereof by an arch bar application instrument for stabilization of said arch bar during bonding thereof to the teeth.

7. An arch bar as recited in claim 1, wherein:
said arch bar is formed from metal sheet stock and said ligature hook elements are integral with said metal sheet stock and bent to a form such that the end portions thereof are disposed in spaced substantially parallel relation with said arch bar and project toward said gingival portion of said arch bar.

8. An arch bar as recited in claim 1, wherein:
said elongated arch bar defines a plurality of apertures along the length thereof for light penetration of said arch bar when photo cure bonding agent is employed for attachment of said arch bar to the teeth of the patient.

9. An arch bar for direct bonding to the teeth of a patient for the management of maxillo-mandibular injuries, comprising:
   (a) an elongated arch bar forming a facial surface a back surface and gingival and occlusal edges and being capable of conforming to the configuration of a desired portion of the buccal and facial surfaces of the teeth of an alveolar arch of the patient and further adapted for contact with a plurality of said teeth, said arch bar forming a plurality of spaced apertures along the length thereof for admission of light therethrough;
   (b) a plurality of ligature hook elements formed integrally with and extending from said occlusal edge of said arch bar and projecting toward said occlusal edge and in spaced relation with said gacial surface and defining a plurality of ligature slots opening toward the gingival; and
   (c) a substantially continuous strip of mesh material being adhered to said back surface of said arch bar and extending substantially along the entire length of said back surface and functioning as a bonding base for bonded fixation of said such bar to the teeth of the patient.

10. An arch bar as recited in claim 9, wherein:
said elongated strip of mesh is composed of metal.

11. An arch bar as recited in claim 10, wherein:
said elongated strip of mesh is adhered to said arch bar by spot welding.

12. An arch bar as recited in claim 10, wherein:
said elongated strip of mesh is adhered to said arch bar by welding.

13. An arch bar as recited in claim 10, wherein:
said elongated strip of mesh is adhered to said arch bar by soldering.

14. An arch bar as recited in claim 9, wherein:
said plurality of ligature hooks are of generally rectangular form to enable secured engagement thereof by an arch bar application instrument for stabilization of said arch bar during bonding thereof to the teeth.

15. An arch bar as recited in claim 10, wherein:
said arch bar is formed from metal sheet stock and said ligature hook elements are integral with said metal sheet stock and bent to a form such that the end portions thereof are disposed in spaced substantially parallel relation with said arch bar and project toward said back surface of said arch bar.

* * * * *